United States Patent [19]

Hall et al.

[11] Patent Number: 4,921,802

[45] Date of Patent: May 1, 1990

[54] PLANT VIRUS CDNA

[75] Inventors: Timothy C. Hall, Madison; L. Sue Loesch-Fries, Stoughton; Nancy P. Jarvis; Richard F. Barker, both of Madison, all of Wis.

[73] Assignee: Pioneer Hi-Bred International, Inc., Johnston, Iowa

[21] Appl. No.: 144,692

[22] Filed: Jan. 13, 1988

Related U.S. Application Data

[63] Continuation of Ser. No. 492,582, May 5, 1983.

[51] Int. Cl.$^5$ .................. C12N 15/00; C12N 7/00; C07H 15/12; C12R 1/41
[52] U.S. Cl. .................................. 435/172.3; 536/27; 435/252.3; 435/235; 435/320; 935/18; 935/72; 935/29
[58] Field of Search ............... 536/27; 435/253, 172.3, 435/320, 252.3, 235

[56] References Cited

U.S. PATENT DOCUMENTS 4,440,859 4/1984 Rutter et al. ..................... 435/172

FOREIGN PATENT DOCUMENTS 0067553 12/1982 European Pat. Off. ......... 435/172.3

OTHER PUBLICATIONS

Maniatis et al, 1982 Molecular Cloning: A Laboratory Manual, Cold Spring Harbor Laboratory, pp. 3-5 and 128-132.
Myers et al. (1977), Proc. Natl. Acad. Sci., USA, 74:2840-2843.
Kacian et al. (1976), Proc. Natl. Acad. Sci., USA, 83:2191-2195.
Ahlquist et al. (1981), J. Mol. Biol., 153:23-28.
Dasgupta et al. (1982), Nucleic Acids Res., 10:703-713.
Takamatsu et al. (1983), Nucleic Acids Res., 11:3767-3778.
Gould et al. (1982), Eur. J. Biochem., 126:217-226.
Brederode, F. T. et al. (1980), Nucleic Acids Res., 8:2213-2223.
Cornellissen, B. J. C. et al. (1983), Nucleic Acids Res., 11:1253-1265.
de Martynoff, G. et al. (1980), Biochim. Biophys. Res. Comms., 93:645-653.
Gould, A. R. et al. (1978), Eur. J. Biochem., 91:269-278.
Hoffmann, L. M. (1983), J. Cell. Biochem. Suppl. 7B:279, 12th Annual UCLA Symposia, Keystone, Colo.
Houwing, C. J. et al. (1978), Biochemistry, 17:2927-2933.
Kacian, D. L. et al. (1976), Proc. Nat. Acad. Sci., U.S.A., 73:3408-3412.
Koper-Zwarthoff, E. C. et al. (1979), Nuclei Acids Res., 7:1887-1900.
Koper-Zwarthoff, E. C. et al. (1980), Nucleic Acids Res., 8:5635-5647.
Marks, M. D., et al. (1983), J. Cell. Biochem. Suppl. 7B:278, 12th Annual UCLA Symposia, Keystone, Colo.
Meyers, J. C., et al. (1978), Proc. Nat. Acad. Sci., U.S.A., 75:5329-5333.
Owens, R. A. et al. (1981), Science, 213:670-672.
Edward A. Sternberg, Cloning of Alfalfa Mosaic Virus (Master's of Science Thesis, University of Wisconsin-Madison, 1982).
Bagdasarian et al., in Drug Resistance in Bacteria, pp. 183-197 (S. Mitsuhashi ed. 1983).
Goelet et al., (1982), Proc. Acad. Natl. Sci., USA, 79:5818-5822.

(List continued on next page.)

Primary Examiner—Charles F. Warren
Assistant Examiner—David T. Fox
Attorney, Agent, or Firm—Greenlee & Associates

[57] ABSTRACT

A method is disclosed for detecting RNA viral infections in plants comprising the isolation of an RNA molecule, e.g., from alfalfa mosaic virus (AMV), production of full-length cDNA transcripts, cloning into plasmids and propgation of the recombinant plasmid. This recombinant DNA plasmid is utilized diagostically to test a plant for infection by a virus, e.g., AMV.

7 Claims, 3 Drawing Sheets

OTHER PUBLICATIONS

Ysebaert et al. (1980), J. Mol. Biol., 143:273–287.
Meshi et al. (1981), Mol. Gen. Genet., 184:20–25.
Myers et al. (1977), Proc. Natl. Acad. Sci., USA, 74:2840–2843.
Cornelissen et al. (1983), Nucl. Acids Res., 11:1253–1265.
Cornelissen et al. (1983), Nucl. Acids Res., 11:3019–3025.
Collins, P. L. and Werta, G. W. (1983), Proc. Natl. Acad. Sci., USA, 80:3208–3212.
Pragnell, I. B. et al. (1979), J. Gen. Virol., 43:1–14.
Weiss, G. B. et al. (1976), J. Biol. Chem., 251:3425–3431.
Xu, N. and Shang, F. (1988), Acta Genet. Sin., 15:382–388.
Kuo, M. Y-P et al. (1989), J. Virol., 63:1945–1950.
Wong, T. C. and Hirano, A. (1987), J. Virol., 61:584–589.
Rice, C. M. et al. (1985), J. Virol., 56:227–239.
Ahlquist, P. et al. (1984), J. Mol. Biol., 172:369–383.
Land et al. (1981), Nucl. Acids Res., 9:2251–2266.
Petty, T. D. et al. (1988), Gene, 74:423–432.
Langereis, K. et al. (1986), Virol., 154:409–414.
Goelet, P. et al. (1982), Proc. Natl. Acad. Sci., 79:5818–5822.

```
                                                    100              200              300              400              500              600              700

GTT TTT ATC TTA CAC ACG CTT GTG CAA GAT AGT TAA TCC ATT TAT TTT CCT TGC GCT TTC CAC AGC ATT ACG TTC CAA TAC TGT GAA GAT TTC ACT A
                                                                    M   R   E   P   L   S   H   A   S   I   Q   E   M   L   R   R   V   V   E   K   Q

TG AAT GCT GAC GCC CAA TCC ACC GAT GCC AGC CTT AGT ATG CGA GAA CCT TTA TCT CAT GCC TCC ATT CAG GAG ATG CTT CGA CGC GTA GTC GAA AAG CA
 M   N   A   D   A   Q   S   T   D   A   S   L   S   M   R   E   P   L   S   H   A   S   I   Q   E   M   L   R   R   V   V   E   K   Q

A GCT GCA GAC GAC ACA ACT GCA ATC GGA AAA GTT TTT TCC GAA GCG GGT GCC TAT GCC CAG GAT GCT CTC CCT TCA GAC AAA GGT GAA GTC TTG AAG
   A   A   D   D   T   T   A   I   G   K   V   F   S   E   A   G   R   A   Y   A   Q   D   A   L   P   S   D   K   G   E   V   L   K

ATA TCC TTT TCC CTG GAC GCC ACG CAA CAA CAA AAC ATA CGC GCC TTT CCT CGA ATT GTA TTT TCA AAC AGT TCG AGT TCT CAC TGT T
 I   S   F   S   L   D   A   T   Q   Q   N   I   L   R   A   N   F   P   R   I   V   F   S   N   S   S   S   S   H   C

TT GCG GCT GCC CAT CGT CTA CTA GAA ACC GAT TTT GTT TAC CGA TGT TTC GGT AAT ACG GTT GAT AGT ATT ATA GAC CTT GGA GGA AAT TTC GTT TCC CA
 F   A   A   A   H   R   L   L   E   T   D   F   V   Y   R   C   F   G   N   T   V   D   S   I   I   D   L   G   G   N   F   V   S   H

T ATG AAG GTA AAG CGG CAT AAT GTA CAT TGC TGC TGT CCC ATA TTG GAT GCT AGA GAC GGA GCT AGG CTC ACG GAG AGA ATA TTG TCT CTA AAG TCG TAC
   M   K   V   K   R   H   N   V   H   C   C   C   P   I   L   D   A   R   D   G   A   R   L   T   E   R   I   L   S   L   K   S   Y

GTC CGA AAA CAC CCG GAA ATT GTG GGA GAA GCA GAT TAC TGC ATG GAC ACG TTT CAG TGC TCA AGG CGA GCT GAC TAT GCT TTT GCC ATC CAT CCT A
 V   R   K   H   P   E   I   V   G   E   A   D   Y   C   M   D   T   F   Q   K   C   S   R   R   A   D   Y   A   F   A   I   H   P
```

```
                                          1500              1600              1700              1800              1900              2000              2100
T CCA GAG ATG TTA TCC CTC CTA GAC AAA GGA GAG AGA TTA TCG ACT GAT GCT GTT TTA AAA GGG TCT GAA GGT CCA ACG TGG TAT TCT GGT CCT ACC TTT
  P   E   M   L   S   L   L   D   K   G   E   R   L   S   T   D   A   V   L   K   G   S   E   G   P   T   W   Y   S   G   P   T   F

TTA AGT GCG CTG GAT AAG GTC AAT GTT CCT GGT GAT TTT GTC GCC AAA GCT CTG TTG TCG TTG CCT AAG AGA GAT TTG AAA TCT CTA TTT TCT AGG TCA G
 L   S   A   L   D   K   V   N   V   P   G   D   F   V   A   K   A   L   L   S   L   P   K   R   D   L   K   S   L   F   S   R   S

CG ACT TCT CAT TCT GAA CGG ACA CCG GTT CAG GAC AGC CCC GTT CGA TGC ACA GAC GGT GTC TTT TAC CCT ATA AGG ATG TTG AAA TGC CTA GG
  A   T   S   H   S   E   R   T   P   V   Q   D   S   P   V   R   C   T   D   G   V   F   Y   P   I   R   M   L   K   C   L   G

A AGT GAC AAA TTT GAG TCG GTC ACT ATA ACT GAT CCT AGA AGT AAC ACG GAA ACC GTG GAT TTA TAC CAT TCT TTT CAA AAG AAA ATT GAA ACG GTT
  S   D   K   F   E   S   V   T   I   T   D   P   R   S   N   T   E   T   V   D   L   Y   H   S   F   Q   K   K   I   E   T   V

TTC TCA TTC ATT CTT GGA AAG ATT GAT GGT CCT TCT CCT CTA ATT TCT GAT CCA GTA TAC TTC CAA TCA CTT GAG GAT GTG TAC TAT GCT GAA TGG CAT C
  F   S   F   I   L   G   K   I   D   G   P   S   P   L   I   S   D   P   V   Y   F   Q   S   L   E   D   V   Y   Y   A   E   W   H

AA GGA AAT GCC ATT GAT GCG TCA AAT TAC GCG CGT ACC CTG TTA GAC GAT ATC AGG AAG CAG AAA GAA GAG AGC TTA AGA GCT AAA GCG AAG GAA GTT GA
  G   N   A   I   D   A   S   N   Y   A   R   T   L   L   D   D   I   R   K   Q   K   E   E   S   L   R   A   K   A   K   E   V   E

A GAT GCT CAA AAA TTA AAT AGA GCA ATT TTG CAA GTT CAT GCC TAT TTG GAA CAT CCA GAT GGA AGA AAA ATC GAA GGA CTG GGG TTG AGT TCT CAG
  D   A   Q   K   L   N   R   A   I   L   Q   V   H   A   Y   L   E   A   H   P   D   G   R   K   I   E   G   L   G   L   S   S   Q

FIG.2-3
```

```
TTC ATC GCA AAA ATC CCC GAG CTT GCA ATT CCA GCA CCA AAA CCG TTA CCT GAA TTC GAG AAG AAC GCA GAA ACT GGC GAA ATT TTG CGT ATC AAT CCT C
 F   I   A   K   I   P   E   L   A   I   P   A   P   K   P   L   P   E   F   E   K   N   A   E   T   G   E   I   L   R   I   N   P                                                              2200

AT TCA GAT GCC ATT CTT GAA GCA ATT GAT TAC TTG AAG TCC ACT TCA GCC AAT TCT ACT ATC ATT ACC TTG AAC AAA TTG GGT GAT CAT TGT CAG TGG ACG AC
    H   S   D   A   I   L   E   A   I   D   Y   L   K   S   T   S   A   N   S   T   I   I   T   L   N   K   L   G   D   H   C   Q   W   T                                                      2300

A AAA GGT CTT GAT GTA GTG TGG GCC GGT GAC GAT AAA CGT CGA GCT TTC ATC CCA AAG AAG AAT ACT TGG GTC GGA CCT ACT GCT AGA AGT TAT CCC CTT
  K   G   L   D   V   V   W   A   G   D   D   K   R   R   A   F   I   P   K   K   N   T   W   V   G   P   T   A   R   S   Y   P   L                                                            2400

GCA AAA TAT GAA AGA GCA ATG AGC AAG GAT GGA TAC GTA ACT CTG AGA TGG GAC GGA GAA GTT CTA GAT GCT AAT TGT GTC AGG AGT TTA TCT CAA TAT G
 A   K   Y   E   R   A   M   S   K   D   G   Y   V   T   L   R   W   D   G   E   V   L   D   A   N   C   V   R   S   L   S   Q   Y                                                              2500

AG ATC GTC TTT GTT GAC CAA TCA TGC GTC AAA GCC TCA GCG GAG CGT ATC ATT CCA AGC CTG GAG AAA GCC CTG CTT GAA GCA CAT TTT TCA GTT AC
    E   I   V   F   V   D   Q   S   C   V   K   A   S   A   E   R   I   I   P   S   L   E   K   A   L   L   E   A   H   F   S   V   T                                                          2600

G ATT GTT GAT GGA GTT GCT GGT TGC GGA AAA ACC ATC AAG CAA ATA GCC CGT TCA TCG GGT CAG GAT GTG GAT TTG ATC CTT ACC AGC AAT CGT
   I   V   D   G   V   A   G   C   G   K   T   I   K   Q   I   A   R   S   S   G   Q   D   V   D   L   I   L   T   S   N   R                                                                   2700

AGC TCT GCC GAT GAG TTA AAA GAA ACC ATC GAT TGT TCA CCG TTG ACA AAG TTG CAT TAC ATT CGT ACC TGT GAT TCT TAC TTG ATG TCT GCC TCG GCG G
 S   S   A   D   E   L   K   E   T   I   D   C   S   P   L   T   K   L   H   Y   I   R   T   C   D   S   Y   L   M   S   A   S   A                                                             2800
```

FIG.2-4

```
                                                        2900          3000          3100          3200          3300          3400          3500
TA AAA GCA CAG AGG TTA ATC TTT GAT GAA TGT TTT TTG CAA CAT GCA GGT TTA GTC TAT GCC GCT ACT TTA GCT GGT TGT AGC GAA GTT ATT GGT TT
 V   K   A   Q   R   L   I   F   D   E   C   F   L   Q   H   A   G   L   V   Y   A   A   T   L   A   G   C   S   E   V   I   G   F

T GGT GAC ACG GAG CAA ATT CCT TTT GTC TCA AGG AAT CCG TCA TTT CGT CAT CAT AAG CTA ACT GGG AAA GTC GAG AGA AAA TTA ATT ACC TGG
   G   D   T   E   Q   I   P   F   V   S   R   N   P   S   F   R   H   H   K   L   T   G   K   V   E   R   K   L   I   T   W

AGA TCC CCA GAT GCC ACC TAT TGC CTT GAA AAG TAT TTT TAC AAG AAC AAA CCG GTG AAG AAT TCC AGA GTA CTA AGA TCT ATC GAA GTT G
 R   S   P   D   A   T   Y   C   L   E   K   Y   F   Y   K   N   K   P   V   K   N   S   R   V   L   R   S   I   E   V

TG CCG ATA AAT TCC CCT GTA AGC GTT GAG AGA AAT ACC GCT TAT TTC TGT CAT ACT CAA GCT CAG GGT AAG ACT TTC GAT AAT GTT TAT TTC TGT CGT TTA ACT CGT ACC TCA ACG AGT CTT ACT
 V   P   I   N   S   P   V   S   V   E   R   N   T   A   L   Y   L   C   H   T   Q   A   E   K   A   V   L   K   A   Q   T   H   L

A AAG GGA TGT GAT AAT ATC TTT ACT CAT GAA GCT CAG GGT AAG ACT TTC GAT AAT GTT TAT TTC TGT CGT TTA ACT CGT ACC TCA ACG AGT CTT ACT
   K   G   C   D   N   I   F   T   H   E   A   Q   G   K   T   F   D   N   V   Y   F   C   R   L   T   R   T   S   T   S   L   T

ACT GGT AGA GAT CCA ATA AAT GGC CCA TGC CAT GGA TTA GTT GCC CTT TCG AGA CAC AAG AAG ACT TTT AAA TAT TTT ACC ATC GCC CAT GAT AGC GAT G
 T   G   R   D   P   I   N   G   P   C   H   G   L   V   A   L   S   R   H   K   K   T   F   K   Y   F   T   I   A   H   D   S   D

AT GTG ATC TAC AAT GCT TGT AGA GAT GCC GGT AAT ACC GAC AGT ATT TTA GCG AGG AGC TAT AAT ACT AAT TTC TGA ATT AGT CAT TGG TAA TTC AA
 D   V   I   Y   N   A   C   R   D   A   G   N   T   D   S   I   L   A   R   S   Y   N   T   N   F   *
```

FIG.2-5

T GCC AAC CTC CAC TGG GTG GAT TAA GGT TGA GGT ATA GAA TCC TAT TCG CTC CTG ATA GGA GAA ATT CTA TAT TGC TTA TAT ACG TGC TTA TGC ACG TAT 3600

ATA AAT GCT CAT GCT AAA TTG CAT GAA TGC CCC TAA GGG ATG C 3643

GGG GGC AAA ACA GAA GCG CTA CCA GTG GCG AAT GTT CAA GAG GTC AAA TTC ATT TCT GAG AAC ATA CCA GTC ATT GAT GAC CTT TAT TAT TCT GAC G
                                                                                                                                 .
AG AAC ATT CCG TTT CAA ATG CCC GCA CCA TTA CTG GAT GAG TTG GGG ATG TTA CCG GAA CTT GGA CCT CTG AAT GAA GAC ATT AAG CCG GT
      M   P   A   P   L   L   D   E   L   G   M   L   P   E   E   L   G   P   L   N   E   I   E   D   I   K   P   V
G GCG GCT CCG ATG ACG TTA CTA TCT GAG TTT AAA GCC TCA GAT AAT GCT AAG CCA CTC GAC ATA GTC GAA ATC ATT CCA GAC GTA AGT CTG ACG AAG CCT
   A   A   P   M   T   L   L   S   E   F   K   A   S   D   N   A   K   P   L   D   I   V   E   I   I   P   D   V   S   L   T   K   P
TAT GAA GCC GTC ATT TCA GGT AAT GAT TGG ATG ACG TTG GGG AGG ATG ATA CCT ACC ACT CCC GTT CCT CTT ACC ATA AGG GAT GTC TTC TCT GGT CTT T
  Y   E   A   V   I   S   G   N   D   W   M   T   L   G   R   M   I   P   T   T   P   V   P   L   T   I   R   D   V   F   F   S   G   L
CT CGG CAT GGA TCG CCG GAA GTG CCG GAA ATC CAG AAT GCT CTT GAT GAG TTT CTT CCG CTC CAT CAT TCA ATT GAT GAT AAG TAC TTT CAG GAA TGG GTT GAA AC
   S   R   H   G   S   P   E   V   P   E   I   Q   N   A   L   D   E   F   L   P   L   H   H   S   I   D   D   K   Y   F   Q   E   W   V   E   T
C TCA GAT AAA TCT CTC GAT GTC GAT CCA TGT CGA ATC GAT CTG AGC GCG TTT TCA ACA ACT GGC AGT CTT CGG AAA ACT GCT ATG AAC CTC GGT TTA AAA
   S   D   K   S   L   D   V   D   P   C   R   I   D   L   S   A   F   S   T   T   G   S   L   R   K   T   A   M   N   L   G   L   K
CCG GTG CAT TAT CCA CAC GTA AGG GCA GTC AAA CTG AAG CCC TAT TGG CCG ATA AAG AAA CGT AAT ATG AAT GTG CCT AAC CTG GGG CAG ATT TAT GAC G
  P   V   H   Y   P   H   V   R   A   V   K   L   K   P   Y   W   P   I   K   K   R   N   M   N   V   P   N   L   G   Q   I   Y   D

TG AAT TCT GTT GCT AAT TCC GTG GAA TTT AAG CTC TTA ACA ACT GTT GTA GAT CCT GAT AAG CTA TGC ATG TTT CCA GAT TTT ATG TCT GAG GGT GAA GT
 V   N   S   V   A   N   S   V   E   F   K   L   L   T   T   V   V   D   P   D   K   L   C   M   F   P   D   F   M   S   E   G   E   V

T TCG TAT TTC CAT GAC TAT ATA GTT GGT AAG AAT CCC GAC CCT GAA TTA TAT TTA GAT CTA GGT GTT CGT TCC ATC GAT AGC TAT AAA CAC ATG ATT
 S   Y   F   H   D   Y   I   V   G   K   N   P   D   P   E   L   Y   L   D   L   G   V   R   S   I   D   S   Y   K   H   M   I

AAA TCC GTG TTA AAG CCC GTT GAA GAT AAT TCT CTG CAC CTA GAA CGG CCG ATG CCA GCA ACC ATA TAC CAT GAT AAA GAT ATC GTG ATG TCA TCA- A
 K   S   V   L   K   P   V   E   D   N   S   L   H   L   E   R   P   M   P   A   T   I   T   Y   H   D   K   D   I   V   M   S   S

CA CCA ATT TTT GCT GCT GCC CGC TTG ATG TTA GTC TTA AGA GAT AAG ATA ACC ATA CCA AGC GGA AGA TTC CAT CAA TTG TTT TCC ATC CAG GAA AGG TTT CTG
 T   P   I   F   A   A   A   K   L   M   L   V   L   R   D   K   I   T   I   P   S   G   R   F   H   Q   L   F   S   I   Q   E   R   F   L

T GAA GCC TTT GAT GCA AGT TTC CAT TTT AAA GAG ATA GAC TTT TCG AAG TTT GAC AAA AGT CAA AAT GAG TTG CAT CAC TTG ATC CAG GAA AGG TTT CTG
 E   A   F   D   A   S   F   H   F   K   E   I   D   F   S   K   F   D   K   S   Q   N   E   L   H   H   L   I   Q   E   R   F   L

AAA TAC TTA GGT ATA CCC AAC GGA TTT CTA ACC TTA TGG TTT AAT GCG CAT AGA CAT AGA CAT AGA CAT AGA AAT GGC GTT TTC TTT AAC GTC G
 K   Y   L   G   I   P   N   G   F   L   T   L   W   F   N   A   H   R   K   S   R   I   S   D   S   K   N   G   V   F   F   N   V

AT TTC CAA CGT CGT ACC GGA GAT GCG CTT ACA TAC TTG GGA AAC ACA ATA GTG ACA TTA GCT TGT CTA TGT CAT GTG TAT GAC TTG ATG GAC CCA AAT GT
 D   F   Q   R   R   T   G   D   A   L   T   Y   L   G   N   T   I   V   T   L   A   C   L   C   H   V   Y   D   L   M   D   P   N   V
```

GTT TTA AAA CCA TTT TCA AAA TAT TCC AAT TCA ACT CAA TTA ACG CTT TTA CAG TGT AAT TCG TAC TTT TCG TAA GTA AGT TTC TGT AAA AGC GTT TCT T

GT TTT AAT TTG GTC TAA CAC GTA ATT CGT ACT CTT CGT GAG TAA GTT GTG TTA GCC ATA CCT ATC CTT TAA ATT TCT GTC AAT TTA AAA AGA AAA TCA TT
                                                                                        M   E   N   T   K   T   N   A

C CCA TTT GCG TAA TTC GTA CTC TTC GTG AGT AAG TTG TAA ATG GAG AAT ACA AAA ATT AAC TCA ATG TCG ATT CTG GGT CCT AAT CAG CTA AAG CTC TGC ACT CAA TTG G
                            S   S   G   M   S   S   I   L   G   P   N   Q   L   K   L   C   T   Q   L

GTG TCT TAT GCT GAG GAA ATG TTA CTA GCT GAT GAA GTT TCA AAA ATT AAC TCA ATG TCG ATT CTG GGT CCT AAT CAG CTA AAG CTC TGC ACT CAA TTG G
V   S   Y   A   E   E   M   L   L   A   D   E   V   S   K   I   N   S   M   S   I   L   G   P   N   Q   L   K   L   C   T   Q   L

TG CTG TCT AAT GGA GCA GCG CCA GTA GTT TTA AGC CTT GTG TCA AAG GAA AAG AAA TCG ATT CTT CCT AAG ATT GGA CAG AGG ATG TA
V   L   S   N   G   A   A   P   V   V   L   S   L   V   S   K   E   K   K   S   I   L   P   K   I   G   Q   R   M   Y

C GTC CAT CAC TCG GCT ATT TAC CTC TTT TAT ATG CCA AAC ATA CTG AAA AGT TCT TCA GGG AGC ATC ACC TTG AAA CTT TTT AAT GAA GCT ACA GGA GAG
V   H   H   S   A   I   Y   L   F   Y   M   P   N   I   L   K   S   S   S   G   S   I   T   L   K   L   F   N   E   A   T   G   E

TTA GTG GAT GTT GAC ACC GAC CAT GAT GCT ACC CAG GCA TGT ATA TTT GCT GGA CGT TAC CCC CGG AGT ATT CTG GCG AAA GAT GCA GCG AAA GGA CAC G
L   V   D   V   D   T   D   H   D   A   T   Q   A   C   I   F   A   G   R   Y   P   R   S   I   L   A   K   D   A   A   K   G   H

AC TTG AAA TTA GTC GTC CAC GCT GTT GCT TCG ACC AAT GCG AAC TCC GCT GTC GGT CTA TAC CCC ATT TGG GAA GAT GAG TTG AGC AGA AAG CAG AT
D   L   K   L   V   V   H   A   V   A   S   T   N   A   N   S   A   V   G   V   L   Y   P   I   W   E   D   E   L   S   R   K   Q   I

C CTC GAA AGG GGT GCC GAT TTC CTA AAG TTT CCA ATT GCT GAG ACC GAG CCA GTC CGC GAT CTC TTA AAT GCT GGG AAG TTG ACG GAC TTT GTT CTT GAT
  L   E   R   G   A   D   F   L   K   F   P   I   A   E   T   E   P   V   R   D   L   L   N   A   G   K   L   T   D   F   V   L   D

AGG ACA AGG TTG GGT GTG GGG TCA AAG AAT GAT CCC AGT CCG GTT CTT TTA GAA CCA AGA GCT AAG ATT ACC GGG AAG ACA AAG GTT TTT ATT CCC G
  R   T   R   L   G   V   G   S   K   N   D   P   S   P   V   L   L   E   P   R   A   K   I   T   G   K   A   K   T   V   F   I   P

AA GGT CCT AGT GTT CCT AAT ACC ACT ATA AAT GGT ATG GCA ACA ACG GTG ATA GAT GCC TCT CCA AAG GGT CTT GGA GTT CCG AAA GGG TTT AC
  E   G   P   S   V   P   N   T   T   I   N   G   M   A   T   T   V   I   D   A   S   P   K   G   L   G   V   P   K   G   F   T

A TAT GAA AGT TTT ATT AAA GAT GAA ATA TTA CCC GAT CAT TGA TCG GTA ATG GGC CGT TTT TAT TTT TCT TTC AAT TAC TTC CATC ATG AGT TC
  Y   E   S   F   I   K   D   E   I   L   P   D   H   *                                                              M   S   S

T TCA CAA AAG AAA GCT GGT GGG AAA GCT AAA GCT GGT AAA CCT ACT AAA CGT TCT CAG AAC TAT GCC TTA CGC AAA GCT CAA CTG CCG AAG CCT CCG GCG TTG
  S   Q   K   K   A   G   G   K   A   K   A   G   K   P   T   K   R   S   Q   N   Y   A   A   L   R   K   A   Q   L   P   K   P   P   A   L

AAA GTC CCG GTT GTA AAA CCG ACG AAT ACT ATA CTG CCA CAG ACG GGC TGC GTG TGG CAA AGC CTC GGG ACC CCT CTG AGT CTG AGC TCT TTT AAT GGG C
  K   V   P   V   V   K   P   T   N   T   I   L   P   Q   T   G   C   V   W   Q   S   L   G   T   P   L   S   L   S   S   F   N   G

TC GGC GTG AGA TTC CTC TAC AGT TTT CTG AAG GAT TTC GCG GGA CCT CGG ATC CTC GAA GAG GAT CTG ATT TAC AGG ATG GTG TTT TCC ATA ACA CCG TC
  L   G   V   R   F   L   Y   S   F   L   K   D   F   A   G   P   R   I   L   E   E   D   L   I   Y   R   M   V   F   S   I   T   P   S
```

```
C TAT GCC ACC TTT TGT CTC ACT GAT GAC GTG ACG ACT GAG GAT GGT AGG GCC GTT GCG CAT GGT AAT CCC ATG CAA GAA TTT CCT CAT GGC GCG TTT  1600
  Y   A   T   F   C   L   T   D   D   V   T   T   E   D   G   R   A   V   A   H   G   N   P   M   Q   E   F   P   H   G   A   F

CAC GCT AAT GAG AAG TTC GGG TTT GAG TTG GTC TTC ACA GCT CCT ACC CAT GCG GGA ATG CAA AAC CAA AAT TTC AAG CAT TCC TAT GCC GTA GCC CTC T  1700
 H   A   N   E   K   F   G   F   E   L   V   F   T   A   P   T   H   A   G   M   Q   N   Q   N   F   K   H   S   Y   A   V   A   L

GT CTG GAC TTC GAC GCG CAG CCT GAG TCT AAA AAT CCC TCA TAC CGA TTC AAC GAA GTT TGG GTC GAG AGA AAG GCG TTC CCG CGA GGG CCC CT  1800
  C   L   D   F   D   A   Q   P   E   S   K   N   P   S   Y   R   F   N   E   V   W   V   E   R   K   A   F   P   R   A   G   P   L

C CGC AGT TTG ATT ACT GTG GGG CTG CTC GAC GAA GCT GAT GAT CTT GAT CGT CAT TGA TGT ACC CCA TTA ATT TGG GAT GCC AAA GTC ATT TGA TGC TGA  1900
  R   S   L   I   T   V   G   L   L   D   E   A   D   D   L   D   R   H   *

CC TCC ACT GGG ATT AAG GTC AAG GTA TGA AGT CCT ATT CGC TCC TGA TAG GAT CGA CTT CAT ATT GCT TAT ATA TGT GCT AAC GCA CAT ATA TAA AT  2000

G CTC ATG CAA AAC TGC ATG AAT GCC CCT AAG GGA TGC  2037
```

PLANT VIRUS CDNA

This application is a continuation of application Ser. No. 492,582, filed May 5, 1983, now abandoned.

FIELD OF THE INVENTION

This invention relates to the occurrence of viral infections in plants and to the efforts of horticulturists and agronomists to combat these infections in economically significant plant species. Virus infections occur in every known plant species and cause significant reductions in the yield and quality of all agricultural and horticultural plant species. The plant industry in no country in the world is exempt from such virally caused damage and no consistent treatment is known to treat or prevent such viral infections. For example, 90% of the cassava plants in Kenya are infected by cassava mosaic virus resulting in an estimated 75% reduction in yield. As another example, in a recent viral epidemic in Ghana, more than one hundred million cacao trees were lost by infection with swollen shoot virus. Many other examples could be given making it evident that viral epidemics and infections have a vast economic significance. The reduction in yield from food crops is also relevant to the steadily increasing human population of the world and to the chronic malnutrition that already exists.

In particular, alfalfa mosaic virus (AMV) has been shown to cause serious diseases in crop yield. This is a significant finding in view of the fact that most alfalfa is produced in the United States, where approximately 30 million acres are planted with this forage crop, than in any other country. In many cases plants infected by AMV show no symptoms making it difficult to measure the occurrence and spread of the disease and therefore to pinpoint the infection as a cause of reduced crop yields. In other cases, the mosaic disease is evident but by that time the virus has almost certainly spread through a large area of plants in a field.

AMV is economically important on alfalfa and on other annual legume crops. Alfalfa can be an overwintering host from which aphids carry the virus. The disease is also spread from alfalfa to other species of crop plants following a build-up of aphid infestation. Alfalfa mosaic virus causes economically important diseases in crop plants such as peppers, potatoes, celery, peas and beans.

Apart from the removal of infected plants and the use of insecticides to kill off the aphids which transmit the virus, there are no practical methods developed for preventing the spread of AMV.

The solution to this problem is to find a method enabling early detection of viral infections in alfalfa plants and other host plants, thus preventing a great deal of damage by the removal of infected plants or elimination of virus transmitting vectors. This invention provides novel compositions useful in a method of detecting viral infections in plants before visible mosaic symptoms have occurred. (see Crill, P., Hagedorn, D. J., and E. W. Hanson (1970) "Alfalfa Mosaic, the Disease and its Virus Incitant"—a literature review Research Bulletin, Research Division, College of Agriculture and Life Sciences, The University of Wisconsin for a general review on the extensive damage cause by AMV). A similar method has been used for the sensitive and rapid diagnosis of potato spindle tuber viroid disease. (See R. A. Owens and T. O. Diener (1981) Science 213: 670–672.)

From the standpoint of molecular biology, rapid advances have been made in the past thirty years commencing with the discovery of DNA structure and continuing to an understanding of how the genetic instructions in DNA are transcribed into the intermediary messenger-RNA and then translated on ribosomes into the unique proteins which are the hallmarks of individual species.

The structure of DNA is briefly described. The components of DNA are four deoxynucleotides (deoxyguanosine monophosphate; deoxycytidine monophosphate; deoxyadenosine monophosphate; and deoxythymidine monophosphate). These deoxynucleotides are linked by the phosphate group of one deoxynucleotide to the 3'-hydroxyl group of the deoxyribose component of the next deoxynucleotide to give very long deoxynucleotide chains. There is no limitation on the sequence of the nucleotides in the chain. The DNA molecule consists of two such chains in a plectonemic coil. The phosphate molecules and the deoxyribose molecules form the backbone of the chain and face outwards from the coil while the bases (quanine (G); cytosine (C); adenine (A); and thymine (T)) occur in inward facing pairs. These base molecules are flat and so the pairs stack on top of each other as in the steps of a ladder. A restriction is that thymine can only occur in a pair with adenine and cytosine can only occur in a pair with guanine. Thus DNA is double stranded and one strand is complementary to the other. The two strands can be separated by heating and the melting temperature depends on the ratio of A-T pairs to G-C pairs. As the proportion of A-T pairs increases, the melting temperature will decrease. Similarly the presence of uncomplementary base pairs in a double-stranded DNA will decrease the melting temperature. Following melting (denaturation) the two complementary strands can be repaired (re-annealed) by slowly decreasing the temperature. At first re-annealing occurs by random correct contacts but, thereafter, spreads rapidly in both directions along the chains between complementary base pairs.

The genetic information of all eukaryotes and prokaryotes is encoded in DNA. The genetic information of most animal viruses is also single-stranded or double-stranded DNA. In contrast the genetic information of most plant viruses is single-stranded RNA. A single stranded RNA molecule differs from a single stranded DNA molecule in two respects. Firstly, the sugar deoxyribose is replaced by ribose and secondly the base thymine is replaced by uracil. To maintain and increase the quantity of an RNA molecule in vitro, it is essential to reverse transcribe the RNA molecule into a double standard cDNA molecule. Furthermore, since many of the most important functional and structural features of single stranded viral RNA molecules are found in the 5'-terminal and 3'-terminal untranslated regions, it is important to obtain a complete cDNA strand. All methods in use up to the present have led to a majority of incomplete cDNA molecules.

Following the discovery of restriction endonucleases which cleave double-stranded DNA and of ligases which repair cleaved DNA, it has been possible to mix DNA fragments from various sources and to re-ligate them together in new, artificial combinations. These new artificial combinations of genes can be incorporated into bacterial cells where they are replicated and in many cases the genes are transcribed into messenger RNA and translated into proteins.

Bacterial cells carry their genetic information in chromosomes. In addition, samll circular pieces of DNA which are usually unnecessary for the survival of the cells are also found in bacterial cells. These small pieces of DNA are named "plasmids" and they can be isolated and cleaved by restriction endonucleases. These cleaved plasmids can then be mixed with DNA from another species (prokaryotic or eukaryotic) which has been cleaved by a restrictive enzyme with the same recognition site. Following religation, it is often found that pieces of foreign DNA have been included in the recirculized plasmids, i.e., recombined DNA. These recombinant plasmids can be incorporated into a bacterial strain where they are increased by replication.

SUMMARY OF THE INVENTION

A method for detection cryptic infections of plants by alfalfa mosaic virus is disclosed. By this method the multipartite RNA molecules of alfalfa mosaic virus are isolated and reverse transcribed to complete cDNA molecules, cloned into plasmids and transformed into a bacterial carrier strain where the recombinant plasmid is propagated. These cloned plasmids can be made radioactive by nick translation. When a plant is to be tesed for a cryptic infection by alfalfa mosaic virus, the RNA from a tissue sample is isolated and bound to a solid support. The radioactive recombinant DNA plasmids are then purified, denatured and hybridized to the bound RNA. If hybridization occurs, the presence of viral RNA is demonstrated even though no overt symptoms of viral infection were present.

BACKGROUND OF THE INVENTION

The present invention relates to the construction of a specific type of probe to be used in the detection of cryptic viral infections of plants at an early stage before the infections have extensively spread through agricultural fields. If such infections are detected early, the spread of such viral infections can be slowed or even stopped by known methods which inclue spraying insecticides.

Alfalfa mosaic virus (AMV) is one of a family of plant viruses (the Tricornaviridae) with a single stranded plus type RNA genome. The genome (excluding the subgenomic RNA molecules) is segmented into three RNA molecules. This family is defined to include: the alfalfa mosaic virus (AMV) group (of which AMV is presently the only member), the ilarviruses, the bromoviruses and the cucumoviruses (van Vloten-Doting, L., R. I. B. Francki, R. W. Fulton, J. M. Kaper and L. C. Lane (1981) Intervirology 15: 198–203). The genome fragments (bottom (B)-, middle (M)-, and top component b(Tb)-RNA) are separately encapsidated in bacilliform particles of different lengths. Besides these three components, a fourth particle (top component a (Ta)) containing two identical sized RNA molecules is found in virus preparations. A mixture of the three genome fragments ((B))-, (M)- and (Tb)-RNA) together with a small amount of coat protein or its messenger, Ta-RNA (Bol, J. F., van Vloten-Doting, L. and Jaspars, E. M. J. (1971) Virology 46: 73–85) is required to initiate infection. Coat protein occurs in polyribosomes extracted from infected leaves and in preparations of the soluble virus replicase, thus indicating that the coat protein has a regulatory function in the translation and/or replication of virus RNA. There is a high degree of homology in the 145 base pairs at the 3'-termini of all four RNAs. (C. J. Houwing and E. M. J. Jaspars (1978) Biochemistry 17: 2927–2933).

The B-, M-, Tb- and Ta-RNA genome fragments are also referred to as RNA 1, RNA 2, RNA 3 and RNA 4, respectively. The complete sequence of AMV RNA 4 has been described (F. T. Brederode, E. C. Koper-Zwarthoff and J. F. Bol (1980) Nucleic Acids Res. 8: 2213–2223). RNA 4 is 881 nucleotides in length. The coding region is 660 nucleotides (not including the initiation and termination codon) flanked by a 5'-noncoding region of 39 nucleotides and a 3'-noncoding region of 182 nucleotides. The sequence of RNA 4 is present in RNA-3 and located at the 3'-end of this RNA species (Gould, A. R. and Symons, R. H. (1978) Eur. J. Biochem. 91: 269–278).

In addition, the complete nucleotide sequence of alfalfa mosaic virus RNA 1 has been published (B. J. C. Cornelissen, F. T. Brederode, R. J. M. Moormann and J. F. Bol (1983) Nucleic Acids Res. 11: 1253–1265). Double stranded cDNA was cloned and the sequence data were obtained from clones with overlapping inserts. The complete sequence is 3645 nucleotides in length and it contains a long open reading frame for a protein of Mw 125,685 flanked by a 5'-terminal sequence of 99 nucleotides and a 3'-noncoding region of 163 nucleotides, including the sequence of 145 nucleotides which the three genomic RNAs of AMV have in common.

A limited amount of information is available on the 5'-terminal and 3'-terminal sequences of AMV RNA 2 and 3. These sequences were obtained by sequencing RNA strands. At the 5'-termini, the sequence of 13 nucleotides of AMV RNA 2 and 101 nucleotides of AMV RNA 3 have been published (E. C. Koper-Zwarthoff, F. T. Brederode, G. Veeneman, J. H. van Boom and J. F. Bol (1980) Nucleic Acids Res. 8: 5635–5647). Extensive homology occurs between the first 11 nucleotides of all four AMV RNAs. AMV RNA 3 is dicistronic and the sequence of 122 nucleotides at the intercistronic junction is known (E. C. Koper-Zwarthoff et al. (1980) Nucleic Acids Res. 8: 5635–5647). Finally the sequences of 227 nucleotides at the 3'-terminus of RNA 3 and of 169 nucleotides at the 3'-terminus of RNA 2 are known (E. C. Zwarthoff, F. T. Brederode, P. Walstra and J. F. Bol (1979) Nucleic Acids Res. 7: 1887–1900). A. R. Gould and R. H. Symons ((1978) Eur. J. Biochem. 91: 269–278) presented evidence that the sequence of AMV RNA 4 is located at the 3'-end of RNA 3.

A comparison of the 3'-terminal sequences of the genomic AMV RNAs (RNA 1, RNA 2 and RNA 3) and of the sub-genomic RNA (RNA 4) has revealed extensive homology between the 3'-terminal 140 to 150 nucleotides of all four RNAs. There are about 20 base substitutions in the 3'-terminal 145 nucleotides of the AMR RNAs but these are either located in the loops of base paired structures or convert A-U base pairs to G-C base pairs in the stems of the secondary structure hairpins (E. C. Koper-Zwarthoff, F. T. Brederode, P. Walstra and J. F. Bol (1979) Nucleic Acids Res. 7: 1887–1900).

RNA sequencing methods are inferior to DNA sequencing methods and so cDNA cloning is a critical tool in molecular biological research. Considerable effort has therefore been made towards optimizing conditions for the preparation of full length cDNA clones. The original approaches to cDNA cloning (Efstradiadis, A., Kafatos, F. C., Maxam, A. M. and Maniatis, T. (1976) Cell 7: 279–288; Rougeon, F. and Mach, B. (1976) Proc. Nat'l. Acad. Sci. U.S.A. 73: 3418–3422) are still in widespread use. By these methods the synthesis of the anticomplementary strand is assumed to be dependent on the formation of a hairpin at the 3'-end of the complementary strand. This hairpin must then be removed by S1 nuclease thereby giving an incomplete cDNA. This is particularly important since the treatment degrades the cDNA corresponding to the 5'-end of the mRNA. Consequently, aspects of an alternate approach originally developed by Rougeon and Mach, supra, which avoids the use of S1 nuclease have been used recently to obtain improved yields of full length clones with intact 5'-ends (Land, H., Grez, M., Hauser, H., Lindemaier, W. and Schutz, G. (1981) Nucleic Acids Research 9: 2251–2266 and Okayama, H. and Berg, P. (1982) Molec. and Cell Biology 2: 161–170). This is achieved by adding a homopolymer tail to the 3'-end of the complementary strand and priming the second strand with the complementary oligonucleotide.

The full implications of the fact that reverse transcriptase can, during the synthesis of the complementary DNA strand, also synthesize the anticomplementary strand (D. L. Kacian and J. C. Meyers (1976) Proc. Nat'l Acad. Sci. U.S.A. 73: 3408–3412) are not generally considered in most cloning schemes. Anticomplementary synthesis has been shown to be largely attributable to an RNAse H activity which resides on the same enzymatic subunit as does the RNA-dependent DNA polymerizing activity (D. P. Grandgennet, G. F. Gerrard and M. G. Green (1973) Proc. Nat'l Acad. Sci. U.S.A. 70: 230–234 and J. C. Meyers, C. Dobkin and S. Spiegelman (1980) Proc. Nat'l Acad. Sci. U.S.A. 77: 1316–1320). After a cDNA-RNA duplex has been formed by the DNA polymerizing activity, the RNA is nicked and degraded into oligoribonucleotides by the RNAs H activity. These oligoribonucleotides are thought to prime the DNA-dependent synthesis of the anticomplementary strand using the complementary strand as a template. Because such priming events occur randomly, the anticomplementary strand consists of a discontinuous series of segments. The inclusion of 4 mM sodium pyrophosphate (NaPPi) in reverse transcriptase reactions reportedly yields longer DNAs. NaPPi has been reported to inhibit RNAse H activity to some extent but does not appear to affect the length of the complementary strand (D. L. Kacian and J. C. Meyers (1976), supra, and J. C. Meyers and S. Spiegelman (1978) Proc. Nat'l. Acad. Sci. U.S.A. 75: 5329–5333). Actinomycin D has also been used to inhibit anticomplementary DNA synthesis; however, it has been reported to be less effective than NaPPi as an inhibitor of RNAase H activity. (D. L. Kacian and J. C. Meyers (1976), supra, and G. De Martynoff, E. Pays and G. Vassart (1980) Biochem. Biophys. Res. Comms. 93: 645–653).

An important consequence of unanticipated anticomplementary DNA synthesis is that it can seriously reduce the probability of obtaining full length cDNA clones if the products of the presumptive first strand reaction (i.e., complementary and anticomplementary DNA) are denatured and submitted to a second synthesis reaction. In such cases, short double stranded DNAs resulting when the anticomplementary strands are rendered double stranded will inevitably outnumber any full anticomplementary strand synthesis. The present invention describes methods whereby these prior art difficulties in obtaining full length cDNA clones are largely overcome.

DNA sequences have been used extensively to probe for specific RNA sequences. For example, the insulin gene has been cloned in a recombinant plasmid and used to detect the presence of insulin mRNA in pancreatic tissue. In another instance cloned early histone genes of sea urchins have been used to detect the presence of specific histone mRNA molecules in various stages of sea urchin embryogenesis. Thus the availability of a specific deoxynucleotide sequence can aid in the detection of a specific RNA either in different organs or at different stages of the life cycle. The specific DNA sequence can be easily maintained and propagated as part of a recombinant plasmid in a bacterial strain.

More specifically, cloned DNA sequences have been used to detect the presence of RNA molecules in plant tissue. For example, cDNA clones have been constructed using mRNA purified from developing endosperms of maize. These cDNA clones have been used to determine relative levels of specific maize zein mRNAs transcribed during maize endosperm development (M. D. Marks and B. A. Larkins (1983) J. Cell. Biochem. Suppl. 7B: 278 12th Annual UCLA Symposia). In a different example, using poly(A) RNA from French bean (*Phaseolus vulgaris*), a cDNA library was constructed and screened with pea lectin cDNA to yield a clone coding for an entire mature lectin peptide. By use of this cloned cDNA, the ontogeny of lectin gene expression in several plant tissues has been studied (L. M. Hoffman (1983) J. Cell Biochem. Suppl. 7B: 279 12th Annual UCLA Symposia).

A sensitive and reliable new method based on hybridization of highly radioactive cDNA to potato spindle tuber viroids (PSTV) has been described (R. A. Owens and T. O. Diener (1981) Science 213: 670–672). The PSTV can be bound to a solid support (e.g., nitrocellulose membrane) and its presence can be detected by autoradiography with the labelled cDNA. Comparison of relative autoradiographic intensities showed that the presence of sap from uninfected tuber sprouts reduced the binding approximately tenfold, but 83–250 μg of PSTV were still easily detectable after hybridization with radioactive cDNA. This amount is equivalent to a concentration of 0.04–0.125 μg PSTV per gram of tuber sprouts. Actively growing potato tissue contains 0.5 μg or more PSTV per gram of tissue (M. A. Pfannenstiel, S. A. Slack and L. C. Lane (1980) Phytopathology 70: 1015). The hybridization method described was therefore adequate to detect PSTV in potato tissue.

A recombinant DNA cloning experiment involves a number of essential steps. Firstly, there must be a method for generating DNA fragments whose ends can be ligated into vector DNA molecules. Secondly, this composite, recombined DNA molecule must be introduced into a host cell in which it can be replicated, i.e., cloned. Thirdly, since a very large number of genes exist in an organism, a method must be found for detecting a specific nucleotide sequence that has been inserted into a vector DNA of a specific recombinant DNA clone. One method has been to isolate mRNA molecules and from these to generate double-stranded complementary DNA (cDNA). In many cases the isolation of a cDNA has been facilitated by using tissues in which specific genes are functional. Thus a large proportion of mRNAs in reticulocyte cells are globin mRNAs and a large proportion of mRNAs from pancreatic islet cells are insulin mRNAs. The majority of mRNAs are polyadenylated at the 3'-ends subsequent to transcription, and this feature can be conveniently used to generate cDNA from mRNA. Oligo(dT), used as a primer, will anneal to the poly(A) tail and reverse transcriptase in the presence of all four deoxynucleoside triphosphates can be used to replicate a complementary single-stranded DNA on the mRNA.

The first product is thus an RNA-DNA hybrid. The RNA strand can then be destroyed by alkaline hydrolysis, to which DNA is resistant, leaving a single-stranded cDNA which can be converted into the double-stranded form in a second DNA polymerase reaction. This reaction depends upon the observation that single-stranded cDNA's can form a transient self-priming structure in which a hairpin loop at the 3' terminus is stabilized by enough base pairing to allow initiation of second strand synthesis. Once initiated, subsequent synthesis of the second strand stabilizes the hairpin. The hairpin is then trimmed away by treatment with the single strand specific nuclease S1, giving rise to a fully duplex molecule which has lost several nucleotide residues corresponding to the 5'-terminus of the RNA strand. This fact serves to emphasize that most cDNAs derived from mRNAs lack portions of the 5'-untranslated termini and that the term "full length" has frequently been used in the prior art to refer to the complete coding region, rather than the complete mRNA nucleotide sequence.

This cDNA molecule can then be tailed with oligo(dC) and annealed with a vector (e.g., pBR322) which has been cut open with a restriction endonuclease (e.g., Pst I) and tailed with oligo(dG). (For further general discussion see Old, R. W. and Primrose, S. B. Principles of gene manipulation—an introduction to genetic engineering (1980) University of California Press). A wide variety of DNA vectors known in the art may be employed as cloning vehicles. The choice of DNA vector to be employed will depend upon considerations known to those of ordinary skill in the art, such as the desired insertion site, selection means, stability and the like. A DNA vector into which cDNA has been inserted is termed herein a recombinant DNA plasmid. The recombinant cDNA plasmid is then transformed into a suitable bacterial host strain where it can be propagated.

The majority of mRNAs in eukaryotes have polyadenylated 3'-tails. In contrast, RNAs of many plant viruses do not have poly-A tails. Thus, in order to construct cDNA's of the plant virus RNA's, it is first necessary to add a poly-A tail. (Sippel, A. E. (1973) Eur. J. Biochem. 37, 31–40).

The cloned cDNA is then multiplied in the bacterial strain. After purification, the cDNA probe is labelled with $^{32}P$ to high specific activity (about $10^8$ cpm/μg) by method known in the art, for example, nick translation (P. W. Rigby, M. Dieckmann, C. Rhodes and P. Berg (1977) J. Mol. Biol. 113: 237). This highly labelled cDNA probe enables detection of restriction fragments of DNA derived from single copy genes or from an infection level of one virus particle per cell. In order to detect specific DNA fragments or RNA molecules, the DNA fragments or RNA molecules are first bound by known methods in a denaturing solution to a solid phase material such as nitrocellulose membranes (E. M. Southern (1975) J. Mol. Biol. 98: 503–517 and P. S. Thomas (1980) Proc. Nat'l Acad. Sci. U.S.A. 77: 5201). The labelled cDNA probe can then also be denatured and added in a re-annealing solution to the surface of the nitrocellulose membrane under conditions where cDNA does not bind to the membrane itself. If the cDNA is complementary to the genomic DNA and to the RNA molecules, it will reanneal to the relevant sequences. The unbound labelled cDNA can then be washed away and the labelled fragments described by radioautography. By this method, fragments of genomic DNA containing specific gene sequences (e.g., globin genes) or specific RNAs (e.g., sea urchin histone mRNAs in embryogenesis) can be identified.

DETAILED DESCRIPTION OF THE INVENTION

Figure 1:
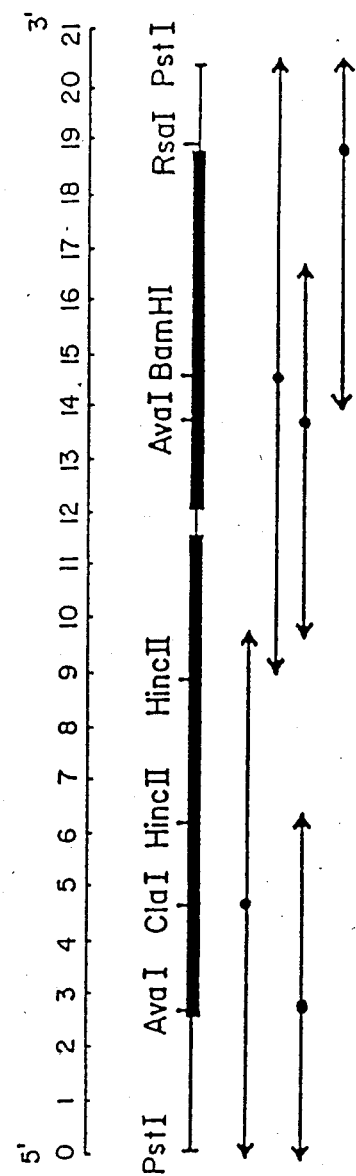

The present invention relates to the construction of circular recombinant DNA plasmids containing a vector and a cDNA sequence for a plant RNA virus, for example, a virus of the Tricornaviridae family. A vector is defined as a circular double-stranded DNA molecule containing a single replicon and all the genes necessary for autonomous replication, and a cDNA sequence is defined as a double-stranded deoxynucleotide sequence replicated by reverse transcription of an RNA molecule. Reverse transcription of an RNA molecule will initially produce an RNA/DNA hybrid which is then converted to a complete double-stranded cDNA sequence by degrading the RNA strand followed by replication of the single-stranded cDNA sequence. In addition, the present invention teaches the utility of the double-stranded cDNA sequences in the detection of viral infections in plants.

The viral RNA was isolated from viral particles under conditions which precluded degradation. Standard methods were available and involved the homogenization of a sample of viral infected plant tissue followed by specific precipitation of the viral particles. Thereafter, the various viral RNA molecules were extracted and the preparation was enriched in genomic RNAs by sucrose density gradient centrifugation. Any extraction method that reliably yields undegraded viral RNA may be employed, and any purification that reliably enriches for the viral RNAs from each other without degradation may be employed.

The purified AMV RNAs were then polyadenylated by addition of approximately 80 adenosine residues to the 3′-ends. Reverse transcription was primed with oligo $(dT)_{12-18}$. Double-stranded DNA was then synthesized and tailed with oligo (dC). This oligo (dc) tailed double-stranded DNA was then annealed to oligo(dG)-tailed pBR322 and transformed into *Escherichia coli* HB 101. pBR322 is a well-known, commercially available vector with a single site for the restriction enzyme PstI. This site was used to linearize pBR322 prior to addition of the oligo(dG) tails used to anneal to the oligo(dC)-tailed cDNA's. *Escherichia coli* HB101 is also a well-known, publicly available bacterial strain which is suitable for progagation of recombinant DNA plasmids because it contains no endogenous restriction endonucleases.

Because previously used methods of forming cDNAs gave few or no full length double stranded cDNAs, the manner in which the known enzymatic properties of reverse transcriptase may limit the length of such full length double stranded cDNAs to be used in cloning was carefully studied. Results showed that the well-documented ability of reverse transcriptase to synthesize anticomplementary DNA prevents the production of full length cDNA clones. When anticomplementary DNA synthesis was inhibited with 4 mM sodium pyrophosphate, the proportion of the cDNA clones that were full length cDNA was significantly increased.

EXAMPLE 1

Isolation of Alfalfa Mosaic Virus Particles

Alfalfa mosaic virus (AMV) was purified from infected *Nicotiana tabacum* L. "Xanthi-nc". 200 g leaves were homogenized in a Waring blender containing 200 ml 0.1M $Na_2HPO_4$, 1% 2-mercaptoethanol and 1 mM ethylene diaminetetraacetic acid (pH adjusted to 7.1 with KOH). 200 ml of a 1:1 solution of chloroform-:butanol was added to the slurry and re-homogenized. The resulting emulsion was centrifuged into an organic and an aqueous fraction. Solid polyethylene glycol was dissolved in the aqueous phase to a final concentration of 5% at which point the viral particles precipitated. [van Vloten-Doting, L. and Jaspars, E. M. J. (1972) Virology 48, 699–708.]

EXAMPLE 2

Isolation of RNA Molecules from Alfalfa Mosaic Virus Particles

[Brakke, M. K. and van Pelt, N. (1970) Anal. Biochem. 38, 56–64.] RNA was prepared by phenol extraction of the virus followed by enrichment for RNAs 1, 2, and 3 by three cycles of linear-log sucrose gradient centrifugation. The presence of the three RNA species can be recognized by electrophoresis (A. C. Peacock and C. W. Dingman (1968) Biochemistry 7: 668–674).

EXAMPLE 3 cDNA Cloning of RNA-1, RNA-2 and RNA-3 from Alfalfa Mosaic Virus

The RNA 1, RNA 2 and RNA 3 enriched fraction of AMV RNA was polyadenylated using a modification of the procedure described [Sippel, A. E. (1973) Eur. J. Biochem. 37, 31–40]. A reaction volume of 70 μl contained 10 mM $MgCl_2$, 2.5 mM $MnCl_2$, 250 mM NaCl, 28 μg bovine serum albumin (BSA), 4 μg viral RNA, 56 nmol ATP, 1.4 units poly(A)polymerase and 2.3 nmol [$^3$H]ATP (20 Ci/nmol) in 50 mM Tris-HCl pH 7.9. This procedure allowed an average of 80 adenosine residues to be added to the 3'-end of RNA-3 in 30 minutes with minimal RNA degradation. The clones listed in Table 1 are on deposit in the Northern Regional Research Laboratory of the U.S. Department of Agriculture and will be made available to the public upon the issuance of this patent.

Basically the synthesis of double stranded cDNA followed H. Land, M. Grez, H. Hauser, W. Lindemaier and G. Schutz ((1981) Nucleic Acids Res. 9: 2251–2266) except for two modifications: (a) Actinomycin D was not included; (b) 4 mM sodium phyrophosphate was included during the synthesis of the first strand. These modifications are believed to be of importance for achieving synthesis of cDNA without loss of any nucleotides of the viral RNA sequences. The double stranded cDNA was not size selected prior to cloning. First strand cDNA was synthesized at 42° C. in a reaction containing 50 mM Tris/Cl (pH 8.3), 200 μM [$\alpha^{32}$P]dcTP (800 uCi/μMole), 500 μM dATP, dGTP and dTTp, 6 mM $MgCl_2$, 400 U/ml placental RNAse inhibitor, 50 μg/ml polyadenylated RNA of AMV, 5 μg/ml oligo (dT), 60 mM KCl, 4 mM sodium pyrophosphate and 400 U/ml reverse transcriptase. After hydrolysis of RNA (0.3N NaOH, 37° C., 4 hr.) and gel filtration on Sephadex G-100, the cDNA was C-tailed using terminal transferase. C-tailed cDNA was rendered double stranded by a second cDNA reaction identical to the first with the exception that oligo(dG) replaced oligo(dT) and placental RNAse inhibitor was deleted. Resulting double stranded cDNA was treated with S1 nuclease and C-tailed again. This oligo(dC) tailed double-stranded cDNA was annealed to PstI-cut, oligo(dG)-tailed pBR322 and transformed into *E. coli* HB101 [Dagert, M. and Ehrlich, S. D. (1979) Gene 6, 23–28]. Samples of tetracycline-resistant, ampicillin-sensitive (Tet$^r$-Amp$^s$) colonies were transferred and bound to nitrocellulose and screened by using 5'-labelled [$^{32}$P]RNA 1, RNA 2, RNA 3, or RNA 4 probes [Grunstein, M. and Wallis, J. (1979) in Methods in Enzymology, Wu, R., Ed. Vol 68, pp. 379–389. Academic Press, New York, NY] excised from a denaturing agarose gel. Colonies that hybridized strongly were selected, plasmid DNA was isolated [Birnboim, H. C. and Doly, J. (1979) Nucleic Acids Res. 7, 1513–1523] and restriction maps of the clones were determined. Full length double stranded cDNA 3 and cDNA 4 inserts into the pBR322 vector were recovered.

EXAMPLE 4

Determination of Nucleotide Sequence of cDNA 1, cDNA 2, cDNA 3 and cDNA 4

As an example, the sequencing strategy for the cDNA 3 clone (pAMV170) derived from AMV RNA 3 is outlined in FIG. 1. The cDNA clone was cut with a suitable restriction enzyme, treated with alkaline phosphatase, and 5'-labelled using polynucleotide kinase. The double end-labelled fragments were then recut with suitable restriction enzymes to produce single end-labelled fragments which were then separated on and eluted from a polyacrylamide gel [see procedures, 4, 5a, 7 and 9 of Maxam, A. M. and Gilbert, W. (1980) in Methods in Enzymology, Grossman, L. and Moldave, K., Eds. Vol. 65, pp. 499–560. Academic Press, New York, NY]. The DNA sequencing reactions were carried out as described but with the following modifications. The limiting G+A reaction was used [Cooke, N. E., Coit, D., Weiner, R. I., Baxter, J. D. and Martial, J. A. (1980) J. Biol. Chem. 255, 6502–6510]. The incubation time for the G reaction was reduced to 30 seconds at 20° C. and the times for the G+A, C+T and C reactions were reduced to three minutes at 20° C. These modifications resulted in increased resolution in the sequence ladders, especially for fragments longer than 400 bases. The electrophoretic system used as a modification of the system previously described [Garoff, H. and Ansorge, W. (1981) Anal. Biochem. 115, 450–457]. Ultra thin gels of 0.2 mm thickness were chemically bonded to one of the glass support plates. Electrophoresis was carried out at a constant temperature of 50° C. maintained at a thermosetting plate. The modified sequencing system used 104 cm×22 cm gels at three polyacrylamide concentrations (4, 6, and 16%). By applying each 5'-labelled fragment to all three concentrations of gel, it was possible to sequence routinely an average of 500 bases per fragment. Computer analysis of the DNA and protein sequences are done using computer programs made available from Drs. O. Smithies and F. Blattner (University of Wisconsin, Madison). The complete nucleotide sequences of cDNA 1, cDNA 2 and cDNA 3 are shown (FIGS. 2–4).

EXAMPLE 5

Detection of cryptic alfalfa mosaic virus infections by use of a cDNA reverse transcribed from an RNA of alfalfa mosaic virus Tissue samples (approximately 0.5 g) are homogenized using a polytron or ground glass homogenizer in 4–5 volumes of cold 50 mM Tris/HCl (pH 8.0), 4% p-amino salicylic acid, 1% tri-isopropylnaphthalene sulfonic acid, 10 mM dithiothreitol (made fresh) and 10 mM Na-metabisulfite (made fresh). n-octanol is used as needed to control foaming. After homgenization, an equal volume of Tris/HCl (pH 8.0)-saturated phenol plus 1% 8-hydroxyquinoline is added and shaken to emulsify. The phases are separated by centrifugation at 20,000–30,000×g for 15 minutes at 4° C. The upper aqueous phase is removed but extracted once with chloroform/octanol (24:1) and centrifuged as above. A concentrated lithium chloride-urea solution to a final concentration of 2M each is added and placed at −20° C. for several hours. The solution turns cloudy immediately. The RNA precipitate is centrifuged down and washed with 2M lithium chloride using a pipette to disperse the pellet. The RNA precipitate is then washed with 76% ethanol-0.3M Na-acetate and dissolved in sufficient water to give a clear solution.

Aliquots (approximately 10 $\mu$l) of the RNA samples are spotted onto nitrocellulose and baked in a vacuum oven at 80° C. for at least 2 hours. The nitrocellulose sheets are then prehybridized at 42° C. for a minimum of 4 hours in 50% formamide, 10% dextran sulfate, 5×standard saline citrate (SSC); 5×Denhardt's solution, 100 $\mu$g/ml denatured carrier DNA, 20 $\mu$g/ml poly(A); 40 mM Na-phosphate (pH 6.8–7.0) and 0.2% sodium dodecyl sulfate.

The double standard cDNA probe is nick translated in the presence of deoxycytidine [$\alpha^{32}$P] triphosphate following a protocol supplied by the Amersham Corporation and yielded an initial specific activity greater than $10^8$ cpm/$\mu$g. The nick translated cDNA probes are denatured by heating for 2 minutes at 100° C. in the presence of 50% formamide before addition to the hybridization reaction. The hybridization reaction is in the same buffer as the prehybridization reaction and is done overnight at 42° C.

Following the hybridization, the nitrocellulose is washed a minimum of three times for 15 minutes at 42° C. with 2×SSC; 25 mM Na-phosphate, 5 mM EDTA and 2 mM Na-pyrophosphate. A further wash for 20 minutes at 64° C. with 1×SSC is then done.

Autoradiography is carried out for 24 to 48 hours at −70° C. with Kodak X-Omat film and DuPont Cronex Lightning-Plus intensifying screens. The persistent occurrence of radioactivity following the extensive washing shows that the tissue sample contained alfalfa mosaic virus RNA strands.

TABLE 1

| Strain | cDNA for AMV RNA component | Plasmid |
|---|---|---|
| NRRL B-15417 | RNA 1 | pAMV212 |
| NRRL B-15418 | 3' end of RNA2 | pAMV34 |
| NRRL B-15419 | 5' sequences of RNA2 | pAMV1A21 |
| NRRL B-15420 | RNA 3 | pAMV39 |
| NRRL B-15421 | RNA 4 | pAMV170 |

What is claimed is:

1. A double-stranded DNA segment comprising the sequence of a complete cDNA derived by reverse transcription of an RNA of alfalfa mosaic virus selected from the group consisting of RNA3 and RNA4.

2. The DNA segment of claim 1 wherein said RNA of alfalfa mosaic virus is RNA4, having a sequence as shown in FIG. 4.

3. The DNA segment of claim 1 wherein said RNA of alfalfa mosaic virus is RNA3, having a sequence as shown in FIG. 4.

4. A recombinant DNA vector comprising a double-stranded DNA segment comprising the sequence of a complete cDNA derived by reverse transcription of an RNA of alfalfa mosaic virus selected from the group consisting of RNA3 and RNA4.

5. A bacterial strain containing and replicating therein the recombinant DNA vector of claim 22.

6. A bacterial strain containing and replicating therein the recombinant DNA vector of claim 4 wherein said RNA is AMV RNA3.

7. A bacterial strain containing and replicating therein the recombinant DNA vector of claim 4 wherein said RNA is AMV RNA4.

* * * * *

UNITED STATES PATENT AND TRADEMARK OFFICE
CERTIFICATE OF CORRECTION

PATENT NO. : 4,921,802

DATED : May 1, 1990

INVENTOR(S) : Timothy C. Hall, L. Sue Loesch-Fries, Nancy P. Jarvis and Richard F. Barker It is certified that error appears in the above-identified patent and that said Letters Patent is hereby corrected as shown below:

The abstract, line 5, please rewrite "propgation" as --propagation--. line 6, please rewrite "diagostically" as --diagnostically--. After the Figures, at column 2, line 24, please rewrite "quanine" as --guanine--. At column 3, line 4, please rewrite "samll" as --small--. At column 3, line 11, please rewrite "restrictive" as --restriction--. At column 3, line 19, please rewrite "detection" as --detecting--. At column 3, line 42, please rewrite "inclue" as --include--. At column 4, line 57, please rewrite "AMR" as --AMV--. At column 5, line 38, please rewrite "RNAs" as --RNAse--. At column 8, line 56, please rewrite "progagation" as --propagation--. At column 9, line 54, please rewrite "phyrophosphate" as --pyrophosphate--. At column 9, line 62, please rewrite "[$\alpha^{32}$P]dcTP" as --[$\alpha^{32}$P]dCTP--. At column 9, line 63, please rewrite "dTTp," as --dTTP,--. At column 11, line 14, please rewrite "homgenization," as --homogenization,--. At column 11, line 40, please rewrite "standard" as --stranded--. At column 12, claim 5, line 40, please rewrite "22" as --4--.

Signed and Sealed this

Eleventh Day of February, 1992

Attest:

HARRY F. MANBECK, JR.

Attesting Officer      Commissioner of Patents and Trademarks